United States Patent [19]

Sato et al.

[11] Patent Number: 4,954,641
[45] Date of Patent: Sep. 4, 1990

[54] NOVEL ANTITUMOR ANTIBIOTIC SUBSTANCE AND A METHOD FOR PRODUCTION THEREOF

[75] Inventors: Yoshikazu Sato; Hiroomi Watabe; Shigetaka Ishii; Tadashi Nakazawa; Takashi Shomura; Masaji Sezaki; Shinichi Kondo, all of Kanagawa, Japan

[73] Assignee: Meiji Seika Kaisha, Ltd., Tokyo, Japan

[21] Appl. No.: 303,230

[22] Filed: Jan. 30, 1989

[30] Foreign Application Priority Data

Jan. 28, 1988 [JP] Japan ................................. 63-15983

[51] Int. Cl.$^5$ .......................................... C07D 311/78
[52] U.S. Cl. .................................................. 549/384
[58] Field of Search ........................................ 549/384

[56] References Cited

U.S. PATENT DOCUMENTS 4,847,387 7/1989 Nakano et al. ...................... 549/384

OTHER PUBLICATIONS

The Journal of Antibiotics, vol. IX, No. 2, pp. 75–81 (1956).
The Journal of Antibiotics, vol. XXIV, No. 9, pp. 599–606 (1971).
Helvetica Chimica Acta, vol. 60, Fasc. 3, pp. 896–906 (1977).
The Journal of Antibiotics, vol. XXIII, No. 7, pp. 354–359 (1970).

*Primary Examiner*—Nicky Chan
*Attorney, Agent, or Firm*—Sughrue, Mion, Zinn, Macpeak & Seas

[57] ABSTRACT

An antibiotic substance represented by formula (I)

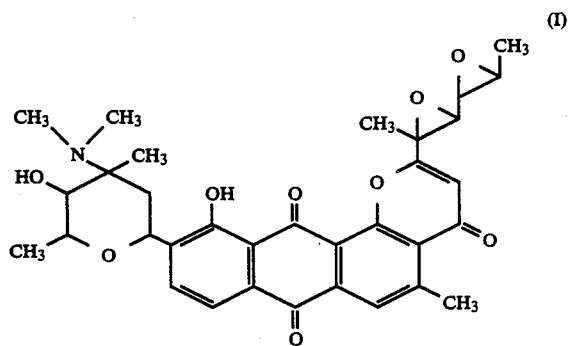

or a pharmaceutically acceptable salt thereof, which is produced by cultivating a microorganism belonging to the genus Streptomyces and isolating the substance from the cultured cells.

1 Claim, 4 Drawing Sheets

NOVEL ANTITUMOR ANTIBIOTIC SUBSTANCE AND A METHOD FOR PRODUCTION THEREOF

FIELD OF THE INVENTION

This invention relates to a novel antitumor antibiotic substance, a pharmaceutically acceptable salt thereof, and a method of producing them.

BACKGROUND OF THE INVENTION

It is known that microorganisms produce a variety of antitumor antibiotics. For example, it has been reported that pluramycin (J. Antibiotics 9A, 75, 1956), neopluramycin (J. Antibiotics 23, 354, 1970), kidamycin (J. Antibiotics 24, 599, 1971) and hedamycin (Helv. Chim. Acta 60, 896, 1977) are all elaborated by microorganisms. However, there is a constant demand for new and better substances having antitumor activity of value-for use as medicines.

To meet the above-mentioned demand, the inventors of this invention made a diligent exploration for substances having antitumor activity and discovered in culture broths of a certain microorganism of the genus Streptomyces a substance having a cytotoxic effect on mouse leukemia cells (P-388) as well as other antitumor and antimicrobial activities. The substance was isolated its physicochemical and biological properties were determined, thus this invention was accomplished.

SUMMARY OF THE INVENTION

An object of this invention is to provide a novel antitumor antibiotic substance (hereinafter referred to as "Substance SF2587")represented by formula (I):

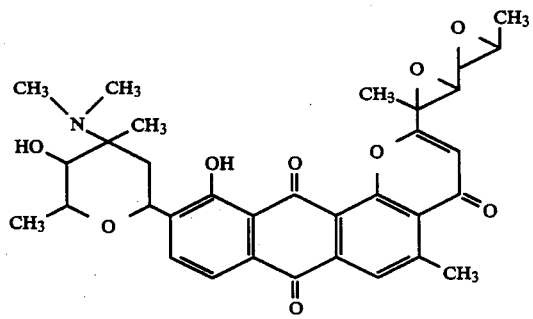

and a pharmaceutically acceptable salt thereof.

Another object of this invention is to provide a method of producing said Substance SF2587 of formula(I) or said salt thereof, which comprises cultivating a Substance SF2587-producing strain of the genus Streptomyces and recovering th substance produced from the cultured cells.

DETAILED DESCRIPTION OF THE INVENTION

Figure 1:
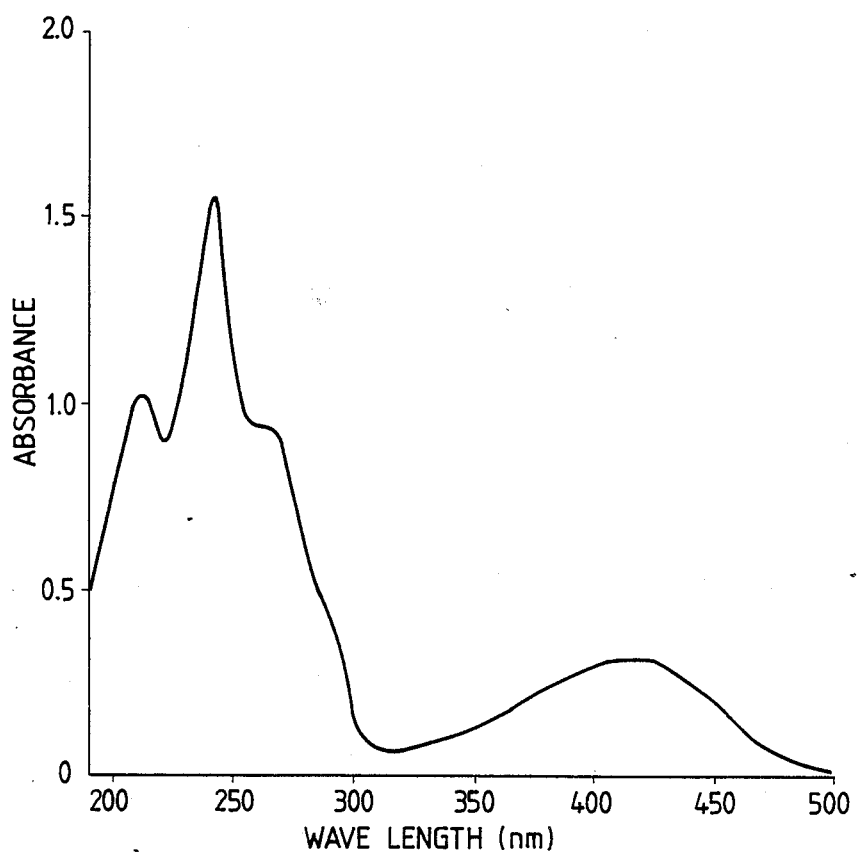
FIG. 1 is an ultraviolet absorption spectrum of Substance SF2587 in methanol.

As an example of the SF2587-producing strain to be used in accordance with this invention, there may be mentioned strain SF2587 which was newly isolated from the soil sample collected in Takatsuki City, Osaka Prefecture (Japan).

The bacteriological characteristics of strain SF2587 are as follows.

I. Morphology

The vegetative mycelium is long-extending and well branched, and is not fragmented under usual conditions. The aerial mycelium is abundant, with good sporulation, on oatmeal agar, inorganic salts-starch agar, yeast extract-malt extract agar, etc. The aerial mycelium is monopodially branched, with no apparent whirl formation. The spore chain at the terminal end of the aerial mycelium is mostly spiral but at times undulating. Electron microscopy reveals that the spore is elipsoidal to cylindrical and measures 0.5 to 0.9×0.7 to 1.3 μm. The spore wall ornamentation is smooth. Usually 20 or more spores occur in chains. The sporangium, motile spore, sclerotium, etc. are not observed.

II. Cultural characteristics

The cultural characteristics of strain SF2587 on various media are shown in Table 1. In the description of color, the color standards given in parentheses are those used in Container Corporation of America's Color Harmony Manual. The observation was made after 14–21 days of incubation at 28° C.

TABLE 1

| Medium | Growth (reverse color) | Aerial mycerium | Soluble pigment |
|---|---|---|---|
| Sucrose nitrate agar | Good, topas (3 ne) | Abundant, gray (2 fe) | None |
| Glucose asparagine agar | Poor-fair, light yellow (2 ec) | None | None |
| Glycerol asparagine agar | Fair, colorless | Fair, gray (3 fe) | None |
| Calcium malate agar | Fair, gray yellow (2 ne) | Abundant, gray (3 fe) | None |
| Inorganic salts-starch agar | Good, rose-beige (4 ge) | Abundant, gray (3 fe) | None |
| Oatmeal agar | Good, rose-beige (4 ge) | Abundant, gray (3 fe) | None |
| Yeast extract-malt extract agar | Good, light brown (3 lg) | Abundant, gray (3 fe) | Pale yellow |
| Tyrosine agar | Fair, tan (3 ie) | Abundant, gray (3 fe) | None |
| Nutrient agar | Fair, topas (3 ne) | Sparse, white | None |
| Bennett agar | Fair, gray yellow (2 gc) | Fair, gray (3 fe) | None |

III. Physiological characteristics
(1) Temperature range for growth: On yeast extract-malt extract agar, growth occurs in the temperature range of 14–45° C. and good growth at 26–37° C.
(2) Liquefaction of gelatin: Positive
(3) Hydrolysis of starch: Positive
(4) Reduction of nitrate: Negative
(5) Peptonization of skimmed milk: Positive Coagulation of skimmed milk: Positive (6) Salt resistance: Growth occurs in media containing 10% NaCl but does not in media containing 12% or more of NaCl.

(7) Production of melanoid pigment: Negative

IV. Utilization of carbon sources (ISP No. 9 medium)

All of D-glucose, glycerol, D-xylose, L-arabinose, L-rhamnose, D-mannitol, D-fructose, raffinose, myo-inositol and sucrose are well assimilated.

V. Cell wall composition

As analyzed by the method of Becker et al. (Appl. Microbiol. 13, 236, 1965), the cell wall fraction contains LL-diaminopimellic acid.

Thus, strain SF2587 is considered to belong to the genus Streptomyces, which is among actinomycetes, with aerial mycelium in the Gray color series, the terminal end of aerial mycelium being mostly spiral, a smooth spore surface, and a reverse color of gray yellow with a tinge of red, and does not produce melanoid pigments.

Accordingly, the inventors of this invention designated strain SF2587 as Streptomyces sp. SF2587.

This strain has been deposited with the Fermentation Research Institute of the Agency of Industrial Science and Technology under the accession number of FERM BP-2244 in accordance with the Budapest treaty.

Like other actinomycetes, strain SF2587 is liable to undergo variation in characteristics. For example, mutant strains (spontaneous or induced) as well as transductants and transformants (genetically engineered) of, or derived from, strain SF2587 can also be used for the purposes of this invention only if they are able to produce Substance SF2587. In the method of this invention, the above-mentioned strain is cultivated in a medium containing the ordinary nutrients which microorganisms may utilize. Thus, as nutrient sources, those known sources which have been conventionally utilized in the culture of actinomycetes can be utilized. For example, as carbon sources, use can be made of glucose, glucose or maltose syrup, dextrin, starch, sucrose, molasses, and animal or vegetable oils, preferably maltose syrup, starch, glucose, soybean oil and sucrose. As nitrogen sources, use can be made of soybean meal, wheat germs, corn steep liquor, cottonseed meal, meat extract, peptone, yeast extract, ammonium sulfate, sodium nitrate, urea and so on, preferably soybean meal and Pharmamedia (trade name of cottonseed meal produced by Troders oil Mill Co., Texas). In addition, it is sometimes advantageous to incorporate various inorganic salts capable of providing sodium, potassium, calcium, magnesium, cobalt, chlorine, phosphate, sulfate and other ions. Preferable examples of inorganic salts include $CaCO_3$, $FeSO_4.7H_2O$ and $CoCl_2.6H_2O$. It is also appropriate to add suitable amounts of organic and/or inorganic substances which assist in the growth of the microorganism and promote production of Substance SF2587. A preferable example thereof is distiller's solubles.

The pH value of the medium preferably ranges from 6.0 to 7.5.

To grow the strain, aerobic culture is carried out, and submerged aerobic culture is particularly advantageous. While the incubation temperature may range from 26 to 37° C., it is appropriate to carry out the cultivation at about 28° C. in many instances. Though it depends on the medium and cultural conditions used, accumulation of Substance SF2587 reaches a peak generally in 2 to 7 days, whether in shake culture or in tank culture (preferably tank culture). When the accumulation of Substance SF2587 has become maximal, the incubation is stopped and the desired substance is isolated and purified from the resulting cultured cells.

Since Substance SF2587 obtained according to this invention is fat-soluble, this property can be exploited in its isolation and purification from the culture broth. Thus, there can be advantageously utilized methods of column chromatography using synthetic adsorbents such as Amberlite XAD-2 (Rhom & Haas Co.), Diaion HP-20 (Mitsubishi Kasei Corporation), etc., gel filtration aids such as Sephadex LH-20 (Pharmacia Fine Chemicals), Toyopearl HW-40 (Tosoh Corporation), etc., silica gel, alumina, etc. or solvent extraction processes using ethyl acetate, chloroform and so on.

By any or a suitable combination of these techniques, Substance SF2587 can be isolated in high purity. The physicochemical properties of Substance SF2587 thus obtained are as follows.

(A) Molecular weight: 589 (EI-MS, m/z 589, M+)

(B) Molecular formula: $C_{33}H_{35}NO_9$ (C) Melting point: Gradual browning from about 224° C., without a definite melting point.

(D) Specific rotation: $[\alpha]_D^{25} = +233°$ (c=0.1, chloroform)

(E) Ultraviolet absorption spectrum: The UV spectrum determined in methanol is shown in FIG. 1.

Figure 2:
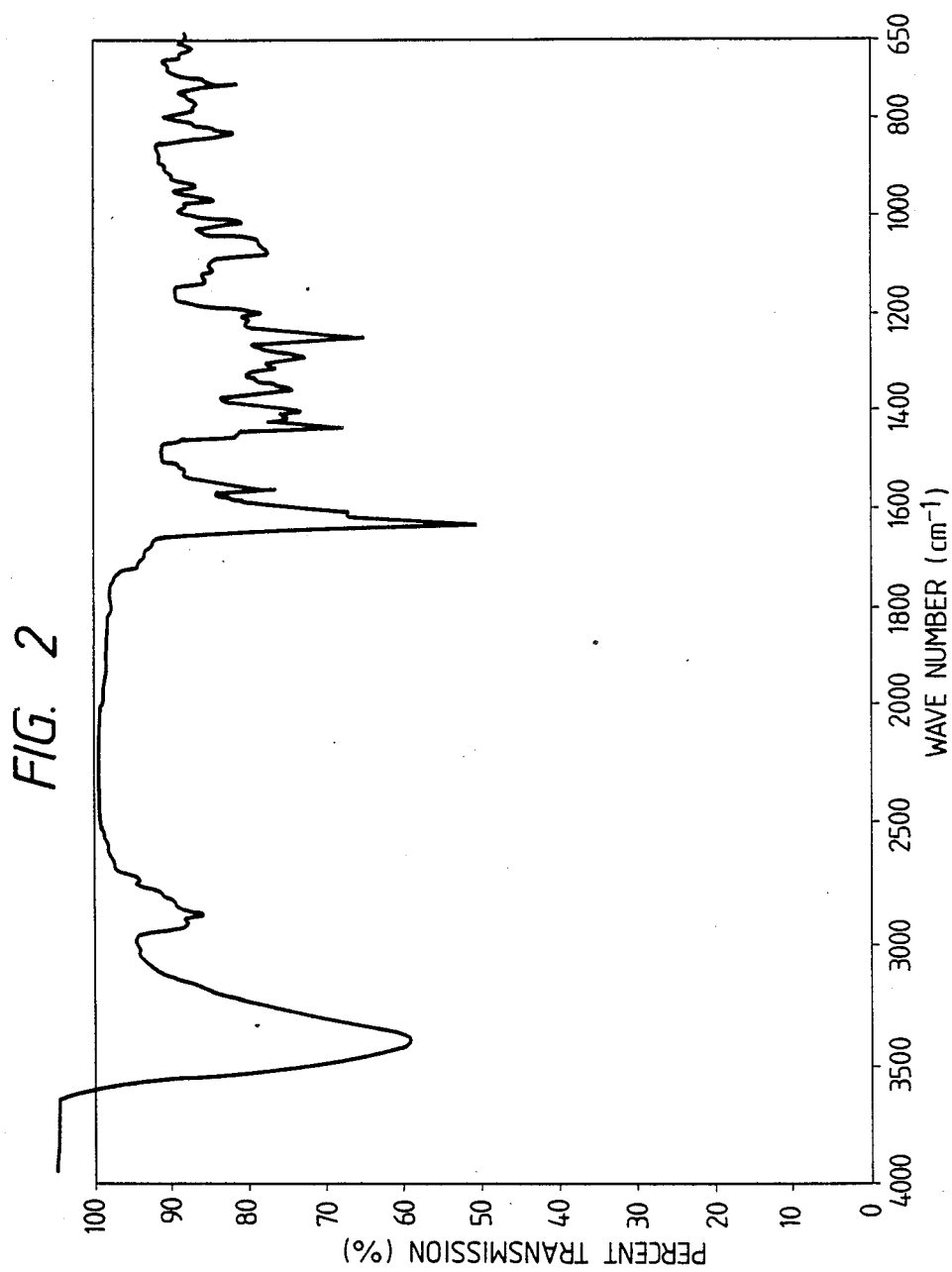
FIG. 2 is an infrared absorption spectrum of Substance SF2587 as determined in a potassium bromide tablet.

(F) Infrared absorption spectrum: The IR spectrum determined in a KBr tablet is shown in FIG. 2.

Figure 3:
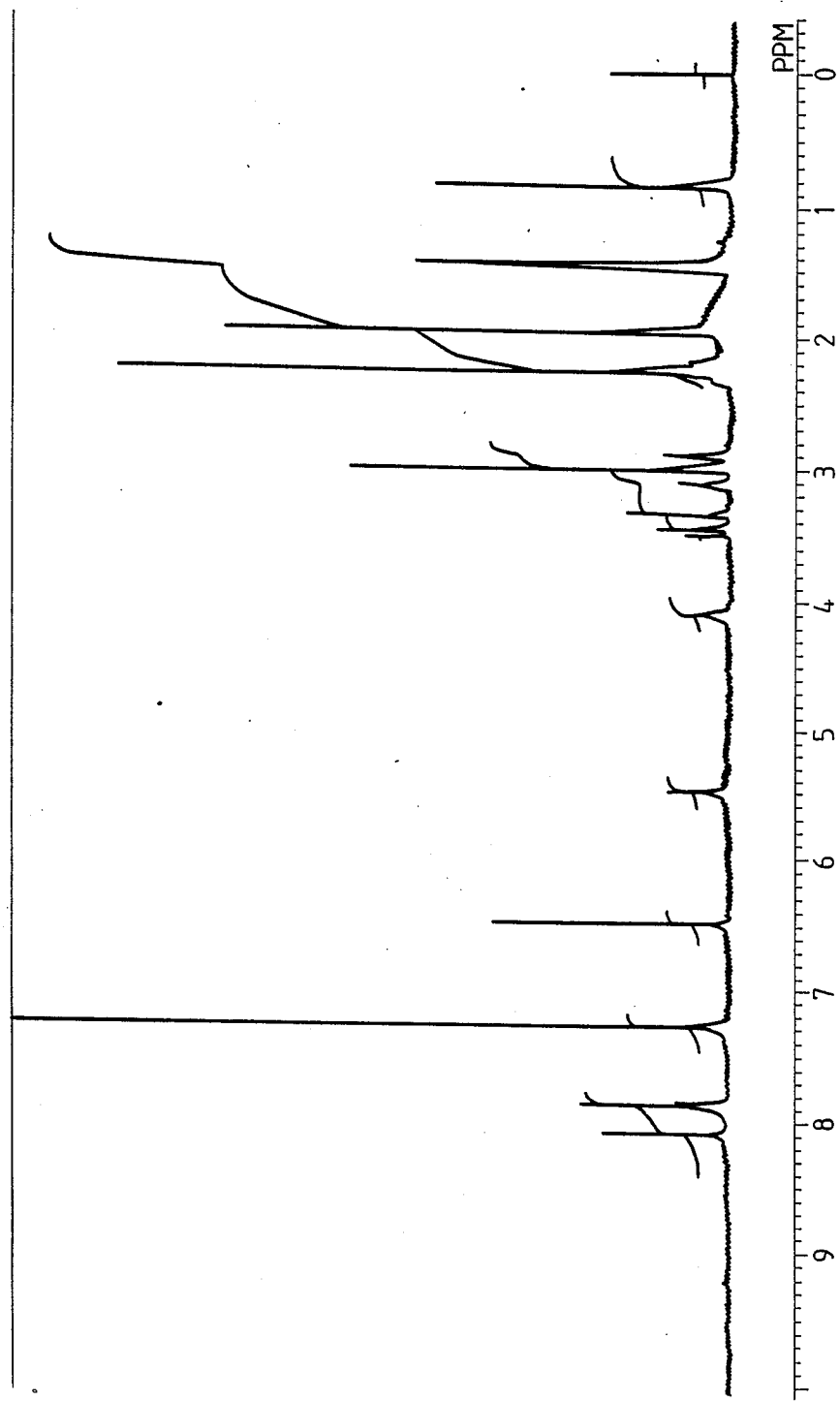
FIG. 3 is a $^1H$ nuclear magnetic resonance spectrum of Substance SF2587 as determined in deuteriochloroform using tetramethylsilane as an internal standard.

(G) $^1H$ nuclear magnetic resonance spectrum: The $^1H$ NMR spectrum determined in deuteriochloroform at 400 MHz is shown in FIG. 3.

Figure 4:
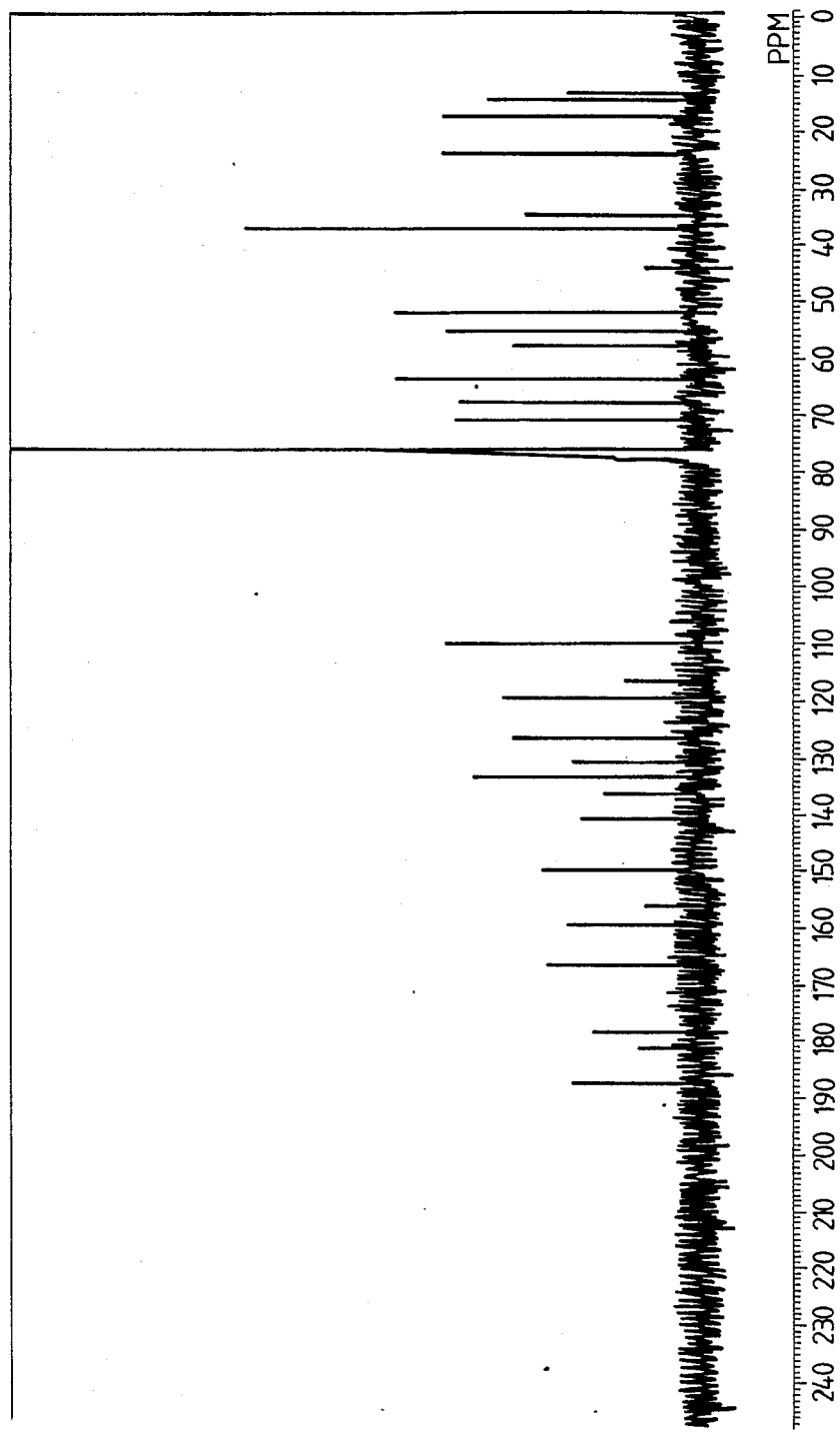
FIG. 4 is a $^{13}C$ nuclear magnetic resonance spectrum of Substance SF2587 as determined in deuteriochloroform using tetramethylsilane as an internal standard.

(H) $^{13}C$ nuclear magnetic resonance spectrum: The $^{13}C$ NMR spectrum determined in deuteriochloroform at 100 MHz is shown in FIG. 4.

(I) Solubility: Soluble in chloroform; only sparingly soluble in methanol, ethanol, ethyl acetate, acetone, diethyl ether and n-hexane; and insoluble in water.

(J) Color reactions: Positive against potassium permanganate, 10% sulfuric acid, and molybdatophosphoric acid reagents. Nagative against ninhydrin reagent.

(K) Thin-layer chromatography: Silica gel thin-layer plate (Merck, Art 5714). The developer solvent systems=chloroform-methanol (5:1):Rf 0.23 and n-butanol-acetic acid-water (4:1:2):Rf 0.37.

(L) Appearance: Yellow powder

Based on the above data and further structural studies, the chemical structure of Substance SF2587 was established to be as represented by formula (I) given hereinbefore.

The biological characteristic of Substance SF2587 are as follows.

(1) Antimicrobial activity

The antibacterial and antifungal activities of Substance SF2587 against various bacteria and fungi were determined by the paper disk method (at 37° C. for 16 hours). The results are shown in Table 2.

TABLE 2

| Concentration (μg/ml) | Diameter of inhibition zone (mm) Test organism | | | | | |
|---|---|---|---|---|---|---|
| | 1 | 2 | 3 | 4 | 5 | 6 |
| 500 | 26.0 | 21.7 | 16.1 | 19.3 | 0 | 0 |
| 125 | 24.2 | 19.1 | 14.1 | 18.0 | 0 | 0 |
| 31 | 19.6 | 14.0 | 11.3 | 13.0 | 0 | 0 |

TABLE 2-continued

| Concentration | Diameter of inhibition zone (mm) Test organism | | | | | |
|---|---|---|---|---|---|---|
| (μg/ml) | 1 | 2 | 3 | 4 | 5 | 6 |
| 8 | 12.4 | 9.8 | 0 | 0 | 0 | 0 |

1. *Micrococcus luteus* ATCC 9341 (gram positive)
2. *Staphylococcus aureus* 209P (gram positive)
3. *Bacillus subtilis* ATCC 6633 (gram positive)
4. *Escherichia coli* NIHJ (gram negative)
5. *Candida albicans* M9001
6. *Candida pseudotropicalis* M9035

(2) Antitumor activity

A Substance SF2587-containing dimethylsulfoxide solution (dimethylsulfoxide concentration: not more than 10%) was administered in a single intraperitoneal dose to mice transplanted i.p. with P-388 tumo cells. After 60 days of feeding, the life span-prolonging effect (T/C%) of Substance SF2587 was determined. The results are shown in Table 3.

TABLE 3

| Dosage (μg/kg) | Antitumor effect P-388 (TIC %) |
|---|---|
| 500 | 226 |
| 250 | 167 |
| 130 | 148 |
| 63 | 133 |

Since, as shown in Table 2, Substance SF2587 according to this invention shows antibacterial activity against gram-positive and gram-negative bacteria, this substance has a potential of use as-an-antibacterial agent. Furthermore, as shown in Table 3, it can be seen that Substance SF2587 has antitumor activity. Therefore, it is also considered to be of value as an antitumor agent.

The salts of Substance SF2587 can be prepared by modifying Substance SF2587 in a conventional manner. Examples of the salts include a hydrochloric acid salt, a hydrobromic acid salt, a sulfuric acid salt, a phosphoric acid salt and an acetic acid salt.

The following example is intended to illustrate this invention and should by no means be construed to be limitative of the invention. It should, of course, be understood that many changes and modifications can be made by those skilled in the art without departing from the scope of this invention.

EXAMPLE

As a seed culture medium, a medium composed of 2.0% starch, 1.0% glucose, 0.6% wheat germ, 0.5% polypeptone, 0.3% yeast extract, 0.2% soybean meal, and 0.2% calcium carbonate was used.

As a production medium, a medium composed of 2.0% maltose syrup, 0.15% soybean oil, 1.0% soybean meal, 0.5% Pharmamedia, 0.25% distiller's solubles, 0.1% calcium carbonate, 0.0005% ferrous sulfate ($7H_2O$), 0.00005% cobalt chloride ($6H_2O$) and 0.00005% nickel chloride ($6H_2O$) was used. Each medium was adjusted to pH 7.0 prior to sterilization.

A 100 ml Erlenmeyer flask containing 20 ml of the above seed culture medium was sterilized at 120° C. for 30 minutes and, then, inoculated with 2-3 loopfuls of Streptomyces sp. SF2587 (FERM BP-2244) grown on an agar slant. The incubation was performed under shaking at 28° C. for 3 days to give a first seed culture. Then, a 500 ml Erlenmeyer flask containing 80 ml of the same seed culture medium as above was sterilized at 120° C. for 30 minutes and, after cooling, inoculated with 2.4 ml of the above-prepared first seed culture. The incubation was carried out under shaking at 28° C. for one day to give a second seed culture.

Four jar fermenters of 50-liter capacity, each containing 35 liters of the production medium which was previously sterilized at 120° C. for 30 minutes were inoculated with 300 ml portions of said second seed culture. The incubation was carried out at 28° C. for 4 days under aeration (20 l/min.) and stirring (250 rpm).

After completion of incubation, the culture broth was filtered with the aid of diatomaceous earth to provide a cell-containing solid fraction.

This solid fraction was extracted with 60l of 67% acetone-water at 20° C. with stirring and, then, filtered to remove the solid matter. This extract was distilled to remove acetone under reduced pressure and 10 l of the resulting concentrate was extracted with 15l of ethyl acetate. The ethyl acetate layer was dehydrated over anhydrous sodium sulfate and concentrated under reduced pressure to give 8.98 g of oil. This oil was evenly mixed with 9 g of diatomaceous earth and dried under reduced pressure for 16 hours. It was then applied to a column in which 400 ml of silica gel C-200 (Wako Pure Chemical Industries) was packed with chloroform. The column was washed with chloroform and chloroform-methanol mixtures (100:1, 50:1, 20:1 and 10:1) in the order mentioned and finally elution was carried out with chloroform-methanol (5:1). The eluate was subjected to the cytotoxicity assay (MTT assay) against mouse leukemia cells (P-388) and the fractions rich in cytotoxicity, which show 50% growth inhibition against P-388 when diluted 1:200, were pooled and concentrated to dryness under reduced pressure to provide 235 mg of oil. This oil was dissolved in a small amount of methanol and applied to a column in which 300 m( of Toyopearl HW-40 (Tosoh coporation) was packed with methanol and elution was carried out with methanol. The eluate was subjected to the cytotoxicity assay using mouse leukimia cells (P-388) and the active fractions, which show 100% growth inhibition against P-388 when diluted 1:122,000, were pooled, concentrated under reduced pressure and allowed to stand at 5° C. for 16 hours. As a result, Substance SF2587 separated out as a yellow precipitate. This precipitate was recovered by filtration and dried under reduced pressure at 40° C. for 16 hours, whereby 3.0 mg of purified Substance SF2587 was obtained as a yellow powder. This product had the physicochemical properties described hereinbefore.

While the invention has been described in detail and with reference to specific embodiments thereof, it will be apparent to one skilled in the art that various changes and modifications can be made therein without departing from the spirit and scope thereof.

What is claimed is:

1. An antibiotic substance represented by formula (I)

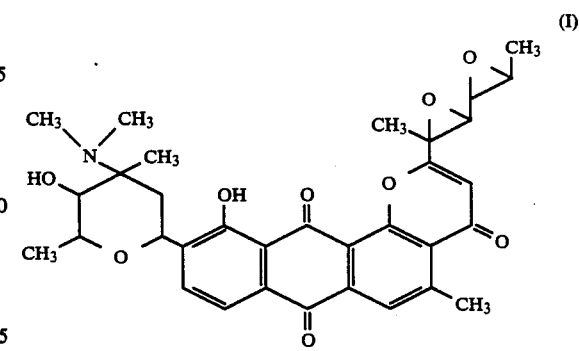

or a pharmaceutically acceptable salt thereof.

* * * * *